United States Patent [19]

Ito et al.

[11] Patent Number: 5,147,187
[45] Date of Patent: Sep. 15, 1992

[54] BLOOD PUMP AND EXTRACORPOREAL BLOOD CIRCULATING APPARATUS

[75] Inventors: Kazuyuki Ito; Takeshi Aizawa; Makoto Tsuneda, all of Tokyo, Japan

[73] Assignee: Nikkiso Co., Ltd., Tokyo, Japan

[21] Appl. No.: 685,268

[22] Filed: Apr. 15, 1991

[30] Foreign Application Priority Data

Apr. 16, 1990 [JP] Japan .................................. 2-99653
Apr. 23, 1990 [JP] Japan .................................. 2-106807
Dec. 25, 1990 [JP] Japan .................................. 2-406111

[51] Int. Cl.⁵ ........................ F04B 17/00; B63H 7/02; F03B 13/00
[52] U.S. Cl. ............................ 417/423.1; 416/223 R; 415/900
[58] Field of Search ................. 417/423.1; 415/223 R, 415/223 B, 206, 900

[56] References Cited

U.S. PATENT DOCUMENTS

| | | | |
|---|---|---|---|
| 3,542,496 | 11/1970 | Bergeson et al. | 417/423.1 |
| 3,697,193 | 10/1972 | Phillips | 415/223 |
| 4,135,253 | 1/1979 | Reich et al. | 417/420 |
| 4,507,048 | 3/1985 | Belenger et al. | 415/90 |
| 4,589,822 | 5/1986 | Clausen et al. | 415/170 |
| 4,606,698 | 8/1986 | Clausen et al. | 415/170 |
| 4,643,641 | 2/1987 | Clausen et al. | 415/170 |
| 5,021,048 | 6/1991 | Buckhotz | 415/900 |

FOREIGN PATENT DOCUMENTS 62-6837 1/1987 Japan .
8600672 1/1986 World Int. Prop. O. .

OTHER PUBLICATIONS

The Japanese Journal of Medical Instrumentation, vol. 56, Suppl. (1986), pp. 10-11, and partial translation.

The Japanese Journal of Artificial Organs, vol. 16, No. 1 (1987), pp. 162-165 and 700, and partial translation.

*Primary Examiner*—Richard A. Bertsch
*Assistant Examiner*—Alfred Basichas
*Attorney, Agent, or Firm*—Browdy and Neimark

[57] ABSTRACT

An extracorporeal blood pump which comprises a pump housing having a pump chamber defined therein, and a rotary vane assembly accommodated within the pump chamber and including a substantially conical rotary pedestal having a base surface and a conical surface, a plurality of vanes each having radially inner and outer ends, and a driven shaft connected at one end with the base surface of the pedestal. The vanes are mounted on the conical surface so as to extend radially outwardly from an axis of rotation of the pedestal with the radially inner ends of the respective vanes being spaced a predetermined equal distance from an apex of the conical surface while substantially depicting a circle coaxial with the axis of rotation of the pedestal. Each neighboring members of the vanes are equally spaced from each other in a direction circumferentially of the pedestal. The base surface has a diameter of 30 to 55 mm enough to substantially cover a surface area of a bottom wall surface which partly defines the pump chamber and confronts the base surface of the pedestal, whereas each of the vanes is in the form of a generally rectangular straight plate extending at an angle of inclination within the range of 20 to 50 degrees relative to an imaginary line tangential to the circle delimited by the radially inner ends of the respective vanes. An extracorporeal blood circulatory device utilizing the blood pump of the type referred to above and comprising a control console accommodating a drive motor for the blood pump is also disclosed.

5 Claims, 9 Drawing Sheets

BLOOD PUMP AND EXTRACORPOREAL BLOOD CIRCULATING APPARATUS

BACKGROUND OF THE INVENTION

1. Field of the Invention

The present invention relates to a blood pump and, more particularly, to the blood pump which is compact and lightweight and easy to manufacture and which can be substantially safely operated for a substantially prolonged length of time without being substantially accompanied by hemolysis while exhibiting a favorable discharge efficiency.

The present invention also relates to an extracorporeal blood circulating apparatus utilizing the blood pump of the type referred to above.

2. Description of the Prior Art

It is well known that a blood pump is extensively used in an extracorporeal blood circulating circuit such as used with, for example, an artificial cardiopulmonary system or an assisted circulatory system for the cardiac function used subsequent to the cardiopulmonary operation. An attempt is now largely being made to use a centrifugal pump as the blood pump for use in the extracorporeal blood circulating circuit.

The centrifugal blood pump generally used in the extracorporeal blood circulating circuit is of a design comprising a pumping chamber communicated with an inflow port on one hand and with an outflow port on the other hand, and a rotary vane assembly accommodated within the pumping chamber for rotation in one direction. This extracorporeal blood pump of centrifugal type is operable to discharge the blood at a controlled rate determined according to the number of revolutions of the vane assembly and the difference between the pressure of the blood supplied to the inflow port of the extracorporeal blood pump and the pressure of the blood discharged from the outflow port of the extracorporeal blood pump, that is, a pressure differential across the extracorporeal blood pump.

The extracorporeal blood pump of the centrifugal type is recognized as being advantageous in that it requires the use of neither expensive artificial valves nor a synchronizing device, both necessitated in a extra corporeal blood pump of pulsating type and can therefore be manufactured compact and light weight at a substantially reduced cost. Also, unlike a peristaltic blood pump comprising a rotor having a plurality of radially outwardly extending arms, each having a roller mounted rotatably on a free end thereof, and operable to successively displace the blood flowing in a flexible tube as the rollers squeeze consecutive portions of the flexible tube during rotation of the rotor, the centrifugal extracorporeal blood pump is known having no problem associated with a fatigue-based failure of the flexible tube and can therefore withstand a prolonged time of use.

Some examples of the prior art centrifugal extracorporeal blood pumps are shown in FIGS. 1 and 2 of the accompanying drawings, respectively, in schematic longitudinal sectional representations, reference to which will now be made for the detailed discussion.

The centrifugal extracorporeal blood pump shown in FIG. 1 comprises a pump housing 16 defining a pump chamber therein and having a blood inflow port defined therein, and a rotary vane assembly rotatably supported within the pump chamber and including a generally disc-shaped pedestal 11 having a generally cylindrical peripheral surface and also having a flat base face at one end and a generally conical top end face opposite to the base face, and a plurality of vanes 12 rigidly mounted on a peripheral edge of the disc-shaped pedestal 11 adjacent the conical top end face so as to extend radially outwardly therefrom. The rotary vane assembly is drivingly coupled with a drive motor (not shown) having a drive shaft 14 connected to the disc-shaped pedestal 11 for rotation together therewith. This prior art centrifugal extracorporeal blood pump shown in FIG. 1 is operable in such a manner that, during the rotation of the rotary vane assembly in one direction driven by the drive motor, the blood entering the inflow port which is generally in alignment with an apex of the shape of the conical top end face of the pedestal 11 is drawn into the pump chamber so as to flow radially outwardly within the pump chamber as indicated by 13.

It has, however, been found that eddy currents, as indicated by 15, of the blood flowing within the pump chamber tend to occur in the vicinity of the outer perimeter of the pedestal 11, imposing relatively large stresses on blood corpuscles to an extent that the blood corpuscles may be destroyed, resulting in hemolysis.

On the other hand, another prior art centrifugal extracorporeal blood pump shown in FIG. 2 comprises a pump housing 19 defining a pump chamber therein and having a blood inflow port defined therein, and a rotary vane assembly rotatably supported within the pump chamber and including a generally disc-shaped pedestal 17 having a flat base face and a generally conical top face opposite to the base face, and a plurality of vanes 18 rigidly mounted on a peripheral portion of the disc-shaped pedestal 17, which is spaced a distance radially outwardly from an apex of the shape of the conical top face, so as to extend radially outwardly therefrom. The rotary vane assembly is drivingly coupled with a drive motor (not shown) having a drive shaft 20 connected to the disc-shaped pedestal 11 for rotation together therewith. This prior art centrifugal extracorporeal blood pump shown in FIG. 2 is operable in such a manner that, during the rotation of the rotary vane assembly in one direction driven by the drive motor, the blood entering the inflow port which is generally in alignment with an apex of the shape of the conical top face of the pedestal 17 is drawn into the pump chamber so as to flow radially outwardly within the pump chamber as indicated by 21.

Again, it has been found that the prior art centrifugal blood pump of the construction shown in FIG. 2 has the following problem. Namely, since the flat base face of the disc-shaped pedestal 17 has a surface area enough to cover the substantially entire bottom surface of the pump housing 19 which confronts the flat base face of the disc-shaped pedestal 17, no eddy current is induced in the flow of the blood being pumped such as occurring in the extracorporeal blood pump shown in and described with reference to FIG. 1. However, even the extracorporeal blood pump shown in FIG. 2 is not only more or less unable to minimize to a satisfactory or required level any possible occurrence of hemolysis, but also tends to exhibit an insufficient blood discharge efficiency.

Also, the extracorporeal blood pump shown in FIG. 2 employs the vanes 18 each being in the form of a curved plate when viewed from top of the pedestal 17, and therefore, it has been difficult to the vane assembly of a type in which the pedestal 17 is integrally formed with the vanes 18.

On the other hand, an extracorporeal blood circulatory device is often used during a medical treatment of a patient, for example, during a cardiac operation or a blood dialysis. The prior art extracorporeal blood circulatory device has the following problems because the drive shaft of the extracorporeal blood pump is coupled direct with the motor drive shaft.

(I) The extracorporeal blood circulatory device is generally required to be so compact and so lightweight that it can be installed bedside and close to a patient lying on a bed and is quiet enough to prevent the patient from being disturbed by noises. However, the prior art extracorporeal blood circulatory device is bulky and heavy in weight and is therefore inconvenient to transport from a storage room to the patient's bedside. Moreover, the drive motor and the movable component parts of the prior art extracorporeal blood circulatory device tend to emit offensive noises and, therefore, it has been recommended to avoid a bedside placement of the extracorporeal blood circulatory device.

Where the bedside setting of the extracorporeal blood circulatory device is inevitable, the extracorporeal blood circulatory device requires noise buffering plates or material to be fitted to the device, resulting in a necessity of the use of a casing of increased size enough to accomodate the noise buffering system. This in turn brings about an increase in size and weight of the extracorporeal blood circulatory system as a whole.

(II) It has often been observed that heat generated from the drive motor used in the extracorporeal blood pump tends to be transmitted from the drive shaft of the motor to the blood flowing within the pump chamber through the drive shaft of the extracorporeal blood pump. Once blood flowing within the pump chamber is heated, the blood is susceptible to hemolysis under the influence of the heat.

SUMMARY OF THE INVENTION

The present invention has been devised to substantially eliminate or minimize the above discussed problems and is intended to provide an improved extracorporeal blood which is compact and lightweight and easy to manufacture, and which can be substantially safely operated for a substantially prolonged length of time without being substantially accompanied by hemolysis while exhibiting a favorable discharge efficiency.

Another important object of the present invention is to provide an improved extracorporeal blood circulatory device which would not substantially emit noises which would disturb a patient, which has a minimized possibility of occurrence of hemolysis and which is substantially lightweight.

To this end, the present invention according to one aspect thereof provides an extracorporeal blood pump which comprises a pump housing having a pump chamber defined therein and also having blood inflow and outflow ports defined therein in communication with the pump chamber, and a rotary vane assembly rotatably accommodated within the pump chamber and including a substantially conicial rotary pedestal having a base surface and a conical surface opposite to the base surface, a plurality of generally elongated plate-like vanes each having radially inner and outer ends opposite to each other, and a driven shaft connected at one end with the base surface of the rotary pedestal. The plate-like vanes are mounted on the conical surface of the rotary pedestal so as to extend radially outwardly from an axis of rotation of the rotary pedestal with the radially inner ends of the respective vanes being spaced a predetermined equal distance from an apex of the shape of the conical surface of the rotary pedestal while substantially depicting a circle coaxial with the axis of rotation of the rotary pedestal, each neighboring members of the plate-like vanes being equally spaced from each other in a direction circumferentially of the rotary pedestal.

The base surface of the rotary pedestal is of a circular shape of a diameter within the range of 30 to 55 mm enough to substantially cover a surface area of a bottom wall surface which partly defines the pump chamber and confronts the base surface of the rotary pedestal, whereas each of the plate-like vanes is in the form of a straight plate of generally rectangular shape and mounted on the conical surface of the rotary pedestal so as to incline at an angle within the range of 20 to 50 degrees relative to an imaginary line tangential to the circle delimited by the radially inner ends of the respective plate-like vanes.

Furthermore, each of the plate-like vanes is so sized that the ratio L/H of the minimum height H in elevation of the radially outer end of each plate-like vane as measured in a direction parallel to the axis of rotation of the rotary pedestal relative to the length L of one of opposite side edges of such plate-like vane which is held in contact with the conical surface of the rotary pedestal is chosen to be within the range of 2.5 to 6.

Preferably, the ratio L/H and the diameter R of the rotary pedestal satisfy the following relationships:

$30 \leq R \leq 55$,
$2.5 \leq L/H \leq 6$,
$L/H \geq 0.133R - 2.33$, and
$L/H \leq 0.133R + 0.51$.

Preferably, the rotary pedestal may have a plurality of blood flow passages each extending from the base surface to the conical surface thereof completely across the rotary pedestal.

In the extracorporeal blood pump embodying the present invention, since the base surface of the rotary pedestal covers a substantially entire bottom surface defining the pump chamber within the pump housing, any possible formation of eddy currents of the blood flowing through the pump chamber can be advantageously eliminated substantially or minimized, consequently resulting in a minimized application of stresses to the flow of the blood.

Also, since the rotary pedestal is of a substantially circular shape and the straight plates serving the vanes are mounted on the conical surface of the rotary pedestal, a smooth flow of the blood can be facilitated and, consequently, no substantial stress which would otherwise result from, for example, a shearing force or the eddy currents act on the flow of the blood within the pump chamber.

Furthermore, since the base surface of the rotary pedestal is of a circular shape having a diameter within the range of 30 to 55 mm, any possible occurrence of hemolysis can be advantageously suppressed.

The selection of the ratio L/H of the minimum height H relative to the length L of that side edge of such plate-like vane within the range of 2.5 to 6 is advantageous in that the blood pump can exhibit a favorable discharge efficiency.

Again, the mounting on the conical surface of the rotary pedestal of each of the plate-like vanes so as to incline at an angle within the range of 20 to 50 degrees relative to an imaginary line tangential to the circle delimited by the radially inner ends of the respective plate-like vanes is effective to suppress the occurrence of hemolysis while allowing the blood pump to exhibit a favorable discharge efficiency.

According to another aspect of the present invention, there is provided an extracorporeal blood circulatory device which comprises an extracorporeal blood pump of the type referred to above. This extracorporeal blood circulatory device may comprise a drive motor having a drive shaft positioned distant from the extracorporeal blood pump and having a drive shaft, and a flexible shaft extending between the driven shaft rigid with the rotary pedestal and the drive shaft of the drive motor.

Preferably, a combination of a detachable coupling and a flexible coupling effective to absorb any possible angular displacement and an eccentric motion of the flexible shaft is interposed between the drive shaft and the flexible shaft and also between the flexible shaft and the driven shaft.

In the practice of the present invention, the driven shaft rigid with the rotary pedestal is not connected direct with the drive shaft of the drive motor. Instead, the drive motor is housed within a control console while it is connected with the driven shaft rigid with the rotary pedestal by means of the flexible shaft.

Unlike the case in which the drive shaft of the drive motor is coupled direct with the driven shaft rigid with the rotary pedestal, the employment of an indirect coupling system in which the drive shaft of the drive motor is connected with the driven shaft rigid with the rotary pedestal by means of the flexible shaft is substantially effective to accomplish a manufacture of the system as a whole in compact and lightweight size.

Accordingly, the centrifugal extracorporeal blood pump can be easy to transport and, because of the compact and light weight features, it can be installed bedside of the patient to be treated.

In addition, since the control console is so designed and so structured as to shield motor-originating noises from being emitted to the outside and, yet, the control console may be positioned at a site distant from the patient's bed, the patent will not be disturbed by the motor-originating noises hitherto encountered.

Noteworthy is that the drive motor which is apt to constitute a source of heat is distant from the centrifugal blood pump, and therefore, any possible occurrence of the hemolysis which would otherwise occur under the influence of heat-based elevated temperature can be advantageously minimized considerably.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined solely by the appended claims. In the accompanying drawings:

DETAILED DESCRIPTION OF THE EMBODIMENTS

Figure 3:
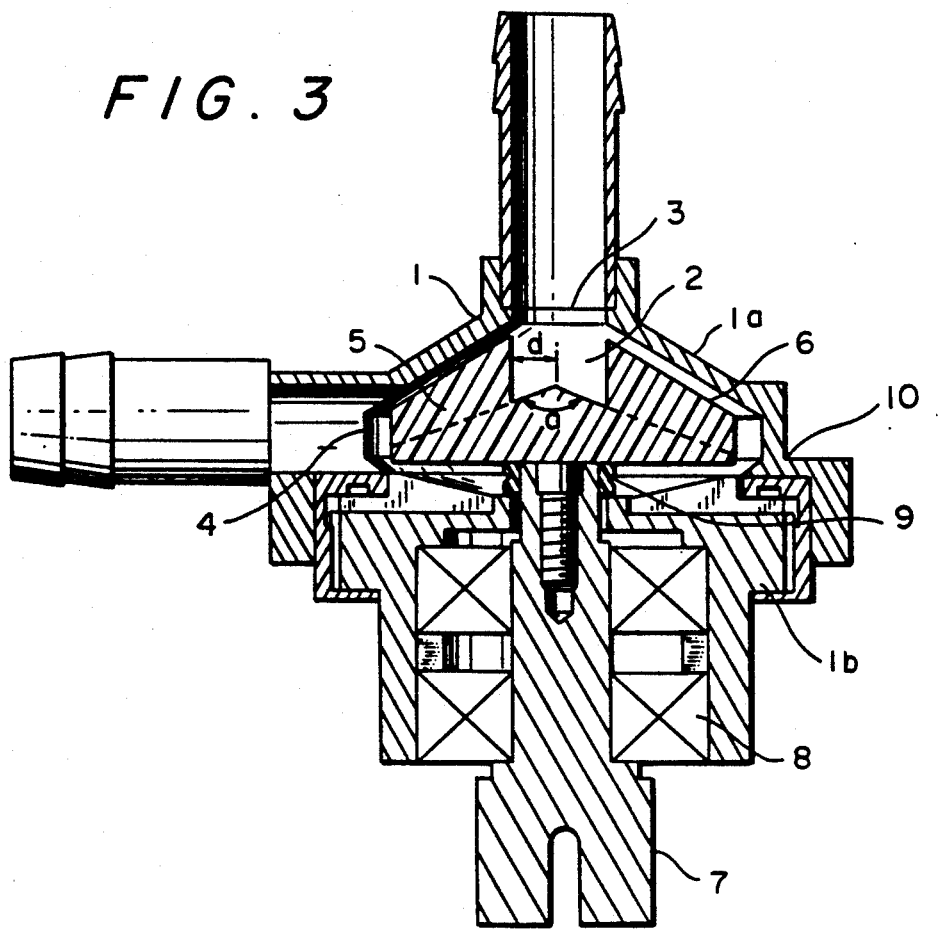
FIG. 3 is a longitudinal sectional view of an extracorporeal blood pump embodying the present invention.

Referring first to FIG. 3 showing, in longitudinal sectional representation, an extracorporeal blood pump embodying the present invention, the blood pump shown therein is referred to as a centrifugal model.

The centrifugal blood pump shown in FIG. 3 comprises a pump housing 1 having a pump chamber 2 defined therein and also having a blood inflow port 3 and a blood outflow port 4 defined therein in communication with the pump chamber 2. The blood pump also comprises a rotary vane assembly including a substantially conical rotary pedestal 5 having a base face and a conical face opposite to the base face and a plurality of vanes 6 mounted on the conical face of the pedestal 5 so as to extend radially outwardly with respect to an axis of rotation of the pedestal 5, each of said vanes 6 being in the form of a straight plate. A driven shaft 7 having one end drivingly coupled with a drive motor (not shown) and the opposite end on which the rotary pedestal 5 is mounted for rotation together therewith is rotatably supported by a bearing assembly 8 and extends through a generally V-sectioned sealing ring 9 used to seal the pump chamber 2. Reference numeral 10 represents an O-ring.

In this structure, during the operation of the extracorporeal blood pump, that is, during the rotation of the rotary vane assembly in one direction, the blood to be pumped from a patient back to the patient via an extracorporeal blood circuit is introduced into the pump chamber 2 through the blood inflow port 3 and is then discharged from the blood outflow port 4 and back to the patient.

Figure 4:
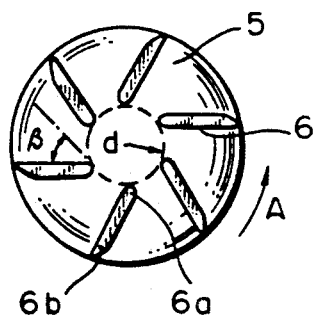
FIG. 4 is schematic top plan view of a rotary vane assembly used in the blood pump of FIG. 3.
Figure 5:
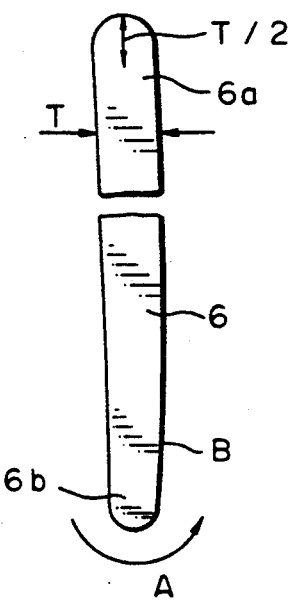
FIG. 5 is a schematic plan view, on an enlarged scale, of one of the vanes used in the rotary vane assembly.

As best shown in FIG. 4, the vanes 6 each being in the form of a generally elongated flat plate are rigidly mounted on the conical face of the substantially conical rotary pedestal 5 with their longitudinal axes extending radially outwardly from the axis of rotation of the rotary pedestal 5, i.e., the longitudinal axis of the driven shaft 7. Specifically, each of the vanes 6 is positioned on the conical face of the rotary pedestal 5 with its inner end 6a (FIGS. 4 and 5) spaced a predetermined distance d radially outwardly from the apex of the conical face of the rotary pedestal 5 and with its outer end terminating in flush with the peripheral edge of the rotary pedestal 5.

Each of the vanes 6 may be made of any suitable material provided that it is lightweight, has a required strength and is effective to minimize hemolysis. For example, each vane 6 may be made of any one of hard plastics such as, for example, polycarbonate resin, polyvinyl resin and polypropylene resin. Of them, the use of polycarbonate resin is preferred as a material for each vane 6.

Preferably, the vanes 6 are integrally formed with the rotary pedestal 5 by the use of any known plastics molding technique and, in such case, the rotary pedestal 5 is made of the same material as that for each vane 6.

Although acrylic resin is considered one of the hard plastics and is generally used in the prior art extracorporeal blood pump, in the practice of the present invention the use of acrylic resin as a material for each vane or for the rotary vane assembly as a whole is undesirable because each vane or the rotary vane assembly made of acrylic resin is susceptible to cracking.

In one preferred embodiment of the present invention, the conical rotary pedestal 5 is of a type having a diameter, specifically a diameter of the base face thereof, within the range of 30 to 55 mm enough for the base face thereof to cover a substantially entire area of an interior bottom wall surface of the housing 1 confronting the base face of the conical rotary pedestal 5. If the conical rotary pedestal 5 is manufactured having the diameter within the above described range, the amount of the blood which may be hemolyzed can be suppressed to a value smaller than 0.1 gram per 100 liters of blood being treated, or occasionally to a value smaller than 0.05 gram per 100 liters of blood being treated.

If the diameter of the rotary pedestal 5 is smaller than the lower limit of 30 mm, the blood being pumped is susceptible to hemolysis. For example, if the diameter of the rotary pedestal 5 is chosen to be 26 mm, the amount of the blood which may be hemolyzed will increase to 0.109 gram per 100 liters of the blood.

On the other hand, if the rotary pedestal 5 has a diameter in excess of the upper limit of 55 mm, the resultant blood pump will require an increased priming volume at the time of start of the blood pump.

As hereinbefore described, the rotary pedestal 5 is of a shape similar to or substantially similar to the shape of a right circular cone with the base face serving the base of the shape of a cone. This conical rotary pedestal 5 has an apex angle $\alpha$ preferably chosen within the range of 120 to 160 degrees. If this apex angle $\alpha$ is greater than the upper limit of 160 degrees, undesirable eddy currents will be induced within the pump chamber 2 during the pumping of the blood through the blood pump.

In the practice of the present invention, each of the vanes 6 satisfies the following requirements.

In the first place, each vane 6 is in the form of a generally elongated straight plate. The use of the generally elongated straight plate for each vane 6 is advantageous in that not only can the integral formation of the rotary pedestal 5 with the vanes 6 be facilitated with no post-production machining substantially required, but also a smooth flow of the blood can occur within the pumping chamber.

The plural vanes 6 are preferred to be circumferentially equally spaced from each other along the conical face of the rotary pedestal 5. The number of the vanes 6 may not be limited if it is plural, however, the use of about six vanes is preferred.

In the second place, as best shown in FIG. 4, the inner end 6a of each vane 6 positioned adjacent the blood inflow port 3 is spaced the predetermined distance d radially outwardly from the apex of the conical face of the rotary pedestal 5 while the inner ends 6a of the respective vanes 6 altogether depict a circle (shown by the phantom line in FIG. 4) of a radius equal to the distance d. In the practice of the present invention, each of the vanes 6 on the conical face of the rotary pedestal 5 is so mounted thereon as to incline an angle $\beta$ relative to an imaginary line tangential to the circle delimited by the inner ends 6a of the respective vane 6, which angle $\beta$ is necessarily chosen to be within the range of 20 to 50 degrees, preferably within the range of 20 to 30 degrees.

If the angle $\beta$ of inclination of each vane 6 relative to the imaginary line tangential to the circle delimited by the inner ends 6a of the respective vane 6 is within the above described range, the resultant blood pump will be effective to minimize the hemolysis while exhibiting a favorable discharge efficiency. Should the angle $\beta$ of inclination be smaller than the lower limit of 20 degrees, the pumping efficiency will be lowered and, on the other hand, should it be greater than the upper limit of 50 degrees, the amount of the blood which may be hemolyzed will increase.

Figure 6:
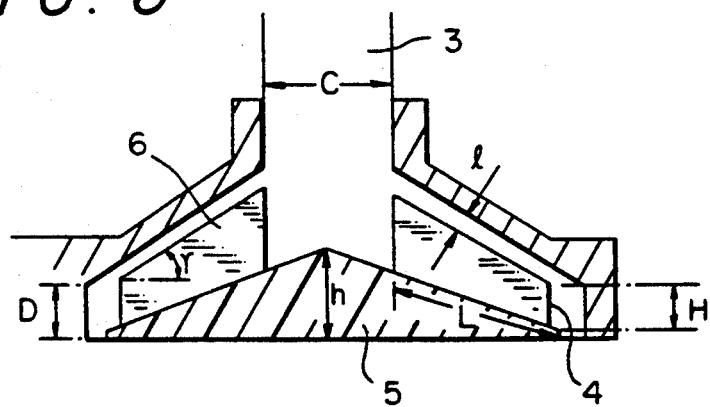
FIG. 6 is a schematic longitudinal sectional view of a portion of the extracorporeal blood pump shown in FIG. 3.

Also, as best shown in FIG. 6, each vane 6 is so shaped and so sized as to exhibit a ratio L/H of the minimum height H in elevation as measured at the respective outer end adjacent the peripheral edge of the rotary pedestal 5 in a direction parallel to the longitudinal axis of the driven shaft 7 relative to the length L of one of opposite side edges of the respective vane 6 which is held in contact with the conical face of the rotary pedestal 5 is necessarily chosen to be within the range of 2.5 to 6.

If this requirement is satisfied, the blood pump constructed in accordance with the present invention can exhibit and maintain a favorable discharge efficiency. However, if the ratio L/H is smaller than the lower limit of 2.5, the amount of the blood which may be hemolyzed will increase, but if the ratio L/H is greater than the upper limit of 6, the pumping efficiency will be lowered.

Furthermore, a more preferable form of each of the vanes 6 is so designed that the diameter R (mm in unit) of the rotary pedestal and the above discussed ratio L/H may satisfy the following relationships, in order to further enhance both of the discharge efficiency and the minimization of the hemolysis.

$30 \leq R \leq 55$, $2.5 \leq L/H \leq 6$, $L/H \geq 0.133 R - 2.33$, and $L/H \leq 0.133 R + 0.51$.

In addition to the foregoing requirements, the blood pump according to the present invention is preferred to satisfy the following additional requirements.

In order to minimize a shearing force, which may act on the flow of the blood across the blood pump, thereby to minimize the hemolysis, the inner end 6a of each vane 6 is preferably rounded, rather than acute-shaped, so as to have a radius of curvature equal to one half of the maximum thickness thereof taken at that inner end 6a and, also, the outer end 6b thereof confronting the blood outflow port 4 is similarly rounded while a portion B of one of opposite side faces of each vane 6, which is situated on a leading side with respect to the direction of rotation of the rotary vane assembly as indicated by the arrow A, is gently curved to terminate at the rounded outer end 6b with the thickness of each vane 6 progressively decreasing from the maximum thickness T to a minimum thickness. It is to be noted that that portion B of the side face of each vane 6, which is gently curved to terminate at the rounded outer end 6b as described above, is a region of the respective vane 6 where the respective vane 6 drastically contacts the blood being pumped.

With the design dimensions of the rotary vane assembly including the diameter of the rotary pedestal 5 having been specified, the present invention has for one of its objects to provide a compact blood pump.

As far as this objective of the present invention be attained, the dimensions of the component parts of the blood pump may not be limited to those shown and described. However, if the compact blood pump capable of giving a maximum blood flow rate of, for example, about 10 liters per minute is desired, it is recommended to employ about 10 mm for the diameter C of the blood inflow port 3 of about 10 mm; 4 to 8 mm for the diameter D of the blood outflow port 4; 6 to 12 mm for the height h of the conical pedestal 5; 0.8 to 1.5 mm for a spacing l delimited between the other of the opposite side edges of each vane 6 remote from the conical face of the rotary pedestal 5 and an inner wall surface of the pump housing 1 confronting the vanes 6; and 30 degrees for an angle $\gamma$ of inclination of that inner wall surface of the pump housing 1.

If the diameter C of the blood inflow port 3 is greater than the upper limit of 13 mm, a problem will occur in that the blood inflow port can not be connected fixedly with pipe in blood circuit used in general extracorporeal blood circulating aparatus, and on the other hand, if the diameter C is smaller than the lower limit of 8 mm, the blood flow will meet with large resistance and it will cause a lot of hemolysis in near site of the blood inflow port 3 and decrease an efficiency of pumping. Similarly, if the diameter D of the blood outflow port 4 is smaller than the lower limit of 4 mm, a problem will occur in that resistance of blood flowing will increase and pumping efficiency will decrease.

Also, where the height h of the rotary pedestal 5 is smaller than the lower limit of 6 mm in case of that the diameter of pedestal 5 is about 50 mm, a problem will occur in that pumping efficiency will decrease and where the height h is greater than the upper limit of 12 mm, a problem will occur in that pumping efficiency will also decrease. In both cases hemolysis tends to increse.

Again, where the spacing l delimited between the other of the opposite side edges of each vane 6 remote from the conical face of the rotary pedestal 5 and the inner wall surface of the pump housing 1 confronting the vanes 6 is smaller than the lower limit of 0.8 mm, a problem will occur in that shear stress against a blood corpuscle will increase, and on the other hand, if the spacing l is greater than the upper limit of 1.5 mm, a problem will occur in that pumping efficiency will decrease.

Finally, if the angle $\gamma$ of inclination of that inner wall surface of the pump housing 1 which defines the spaing l in cooperation with the other of the opposite side edges of each vane 6 remote from the conical face of the rotary pedestal 5 is smaller than the lower limit of 20 degree, a problem will occur in that pumping efficiency will decrease and if it is greater than 40 degree, a problem will occur in that eddy currents will be induced within the pump champer 2.

The details of the blood pump according to the present invention may not be always limited to those shown and described with reference to FIGS. 3 to 6, but may be modified is some ways. For example, the rotary pedestal 5 may have an arbitrarily chosen number of blood flow passages defined therein so as to extend from the base face to the conical face thereof completely across the height thereof. So long as the rotary vane assembly is of a type satisfying the preferred dimensions discussed hereinbefore, the number of blood flow passage to be defined in the rotary pedestal 5 is 6, with each blood flow passage having a diameter within the range of 2 to 4 mm.

Figure 7:
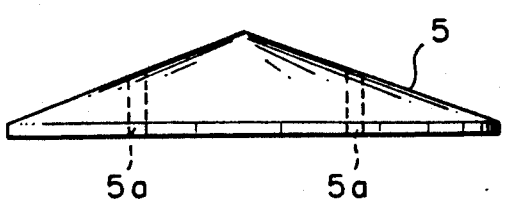
FIG. 7 is a schematic side view of a modified form of a pedestal forming a part of the rotary vane assembly.

One example of the modified form of the rotary pedestal 5 is shown in FIG. 7, wherein two blood flow passages are employed as generally identified by 5a.

In addition, the pump housing 1 may be of two-piece construction including an upper housing portion 1a encompassing the rotary vane assembly and a lower housing portion 1b carrying the driven shaft 7, said upper housing portion 1a serving as a cap adapted to be detachably mounted on the lower housing portion 1b to define the pump chamber 2 therebetween.

Also, instead of the use of the generally V-sectioned sealing ring 9 and the O-ring 10, any suitable sealing systems such as an oil seal, a mechanical seal and/or a modified form thereof may be employed.

To demonstrate the superiority of the blood pump according to the present invention to the comparable prior art blood pump, the present invention will now be described by way of non-limiting examples which are taken only for the purpose of illustration.

EXAMPLE 1

Using the blood pump of the construction shown in and described with reference to FIGS. 3 to 6, a hemolytic test was conducted to determine the amount of the blood hemolyzed.

Particulars of the rotary vane assembly used in the blood pump employed for the test are as follows:

| Material: | Polycarbonate resin |
|---|---|
| Pedestal Diameter R: | 36 mm |
| Pedestal Height h: | 7.5 mm |
| Vane Inclination Angle $\beta$: | 20 deg. |
| Vane Length/Vane Height (L/H) | 3.5 |
| Number of Vanes: | 6 |

The hemolytic test was conducted under the following conditions.

(a) The difference in pressure between the blood inflow and outflow ports of the blood pump, that is, the pressure differential across the blood pump, was fixed at 100 mmHg.

(b) The blood pumping rates employed in the hemolysis test were 1, 2, 3, 4 and 5 liter per minute, respectively.

It is to be noted that this range of blood pumping rate is the range which is frequently employed for the amount of blood passed through an extracorporeal blood circuit used in association with a post-operative ventricular assist device.

(c) During a five-hour continuous run of the blood pump, samples were extracted at intervals of 30 minutes and were tested to determine the amount of free hemoglobin in the plasma according to SLS hemoglobin measurement, thereby to calculate the index of hemolysis (I.H.).

It is to be noted that the index of hemolysis represents a change in quantity of free hemoglobin for each pump discharge rate of 100 liters and the index of hemolysis of not greater than 0.1 gram is recognized as tolerated for biological application.

Figure 8:
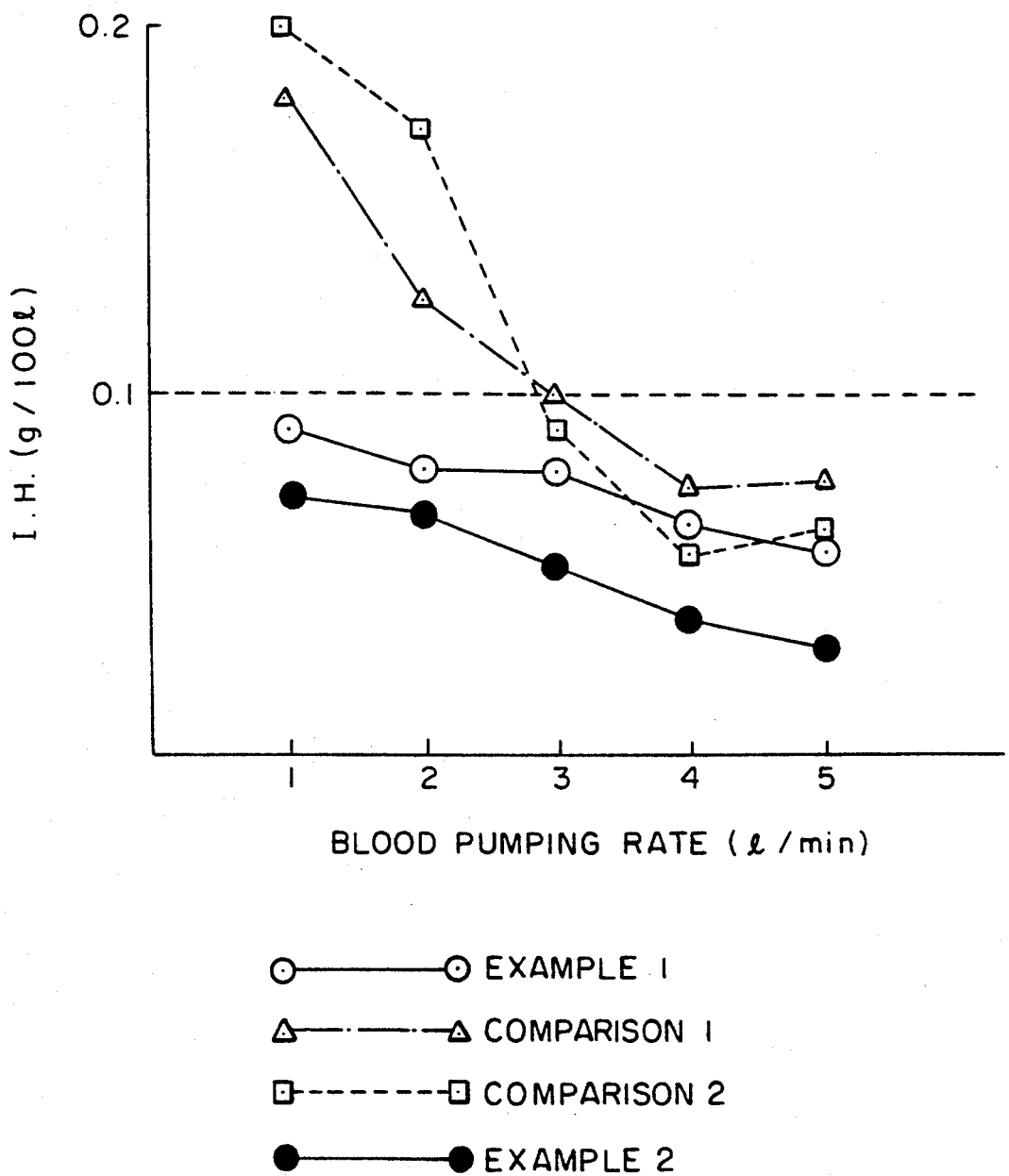
FIG. 8 is a graph showing results of hemolytic tests conducted with the use of the prior art extracorporeal blood pump and that of the present invention.

Results of the hemolytic test are shown in the graph of FIG. 8.

Figure 9:
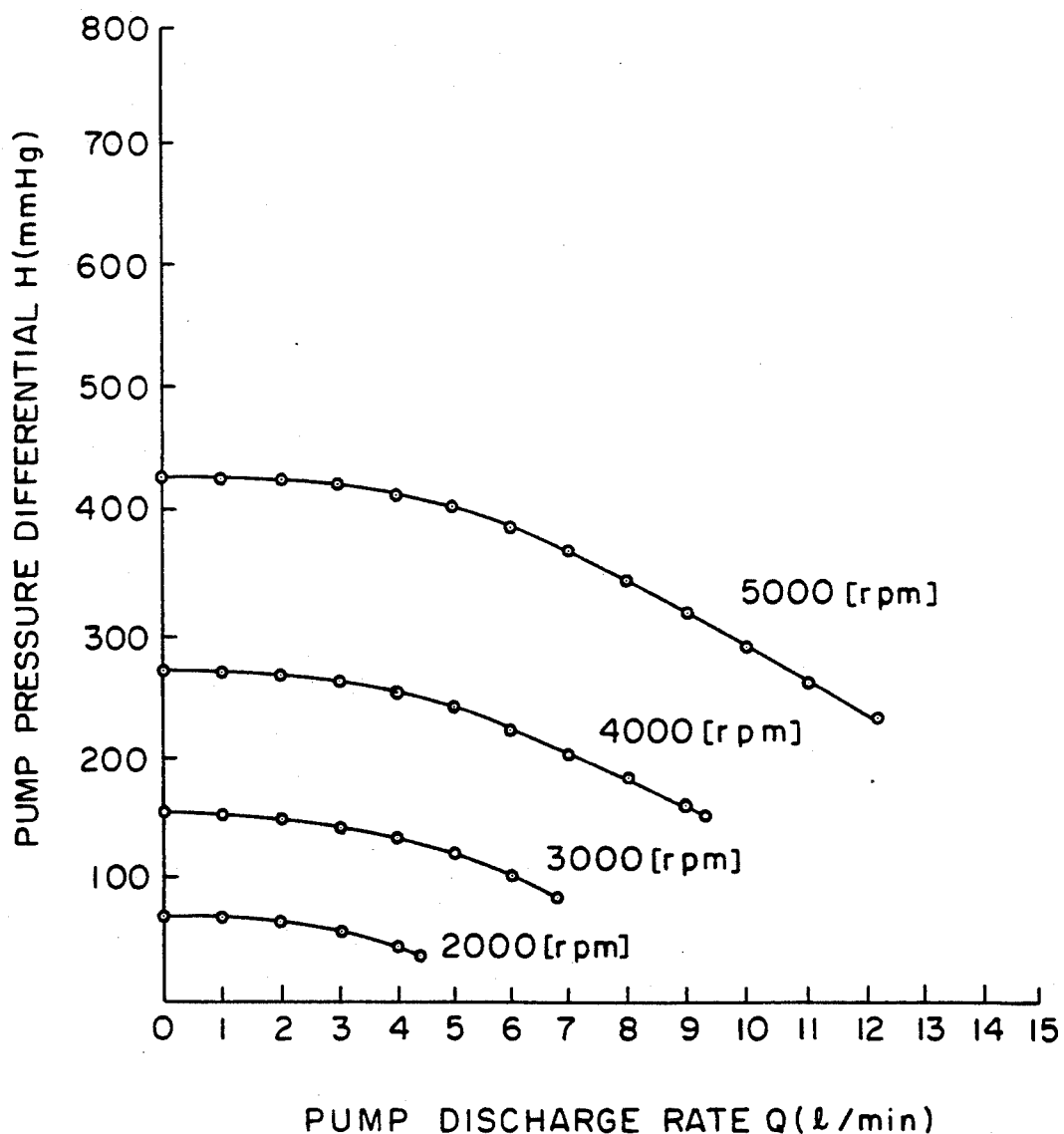
FIG. 9 is a graph showing the discharge characteristic of the extracorporeal blood pump according to the present invention.

Also, output characteristics of the blood pump according to the present invention, including the pump discharge rate and the pressure differential across the blood pump were also examined by driving the blood pump, results of which are shown in the graph of FIG. 9.

COMPARISON 1

Figure 1:
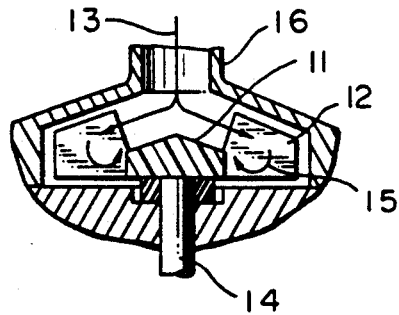
FIG. 1 is a schematic longitudinal sectional view of one type of the prior art extracorporeal blood pump.

Not only was the hemolytic test conducted under the identical conditions with those in Example 1 above with the use of the prior art blood pump of the construction shown in and described with reference to FIG. 1, but also output characteristics of the prior art blood pump were also examined. It is to be noted that the dimensions of the rotary vane assembly used in the prior art blood pump and the type of material used to construct such rotary vane assembly were identical with those of the rotary vane assembly used in the blood pump in Example 1.

Figure 10:
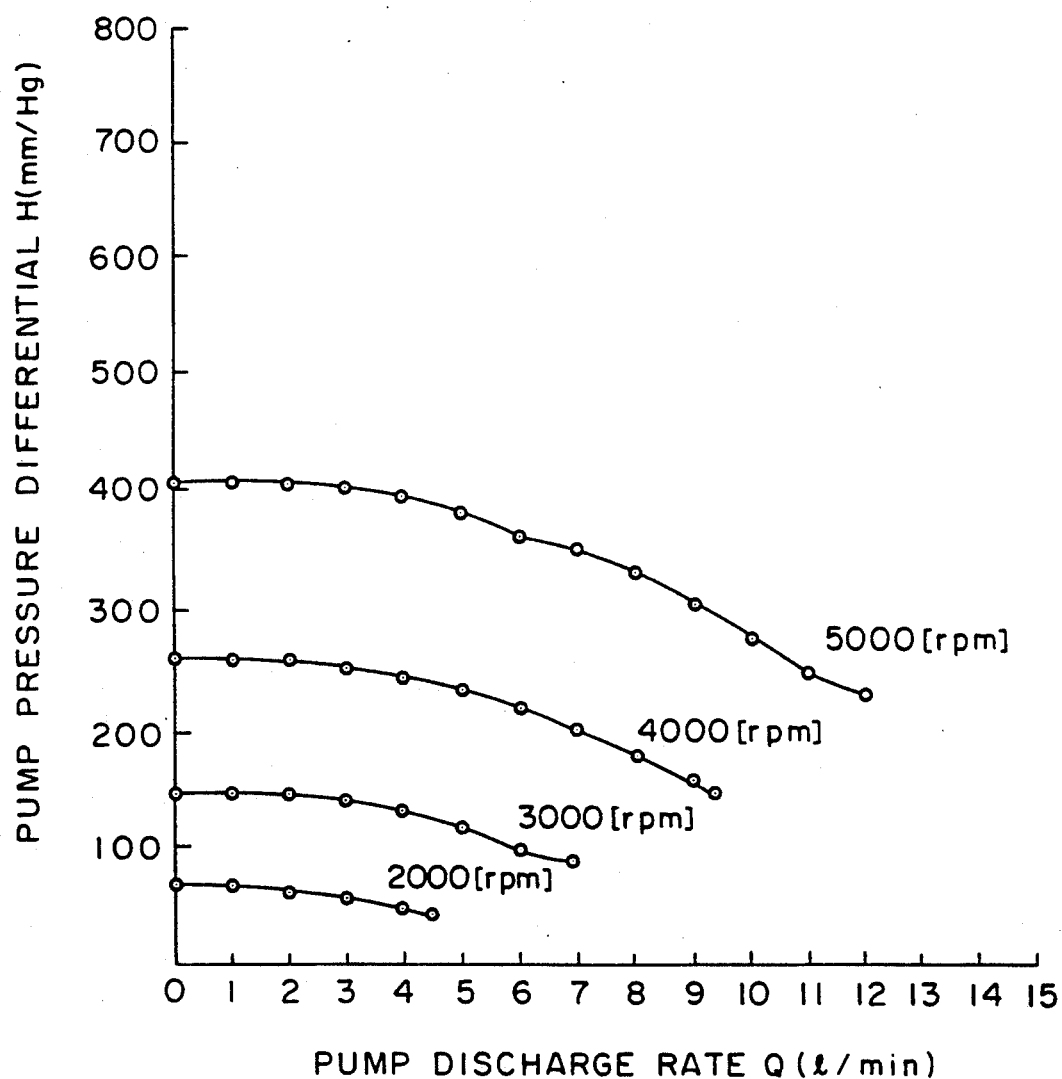
FIG. 10 is a graph showing the discharge characteristic of the prior art extracorporeal blood pump used in Comparison 1.

Results of the hemolytic test and the measured output characteristics both associated with the prior art blood pump are shown in the respective graphs of FIGS. 8 and 10.

COMPARISON 2

Figure 2:
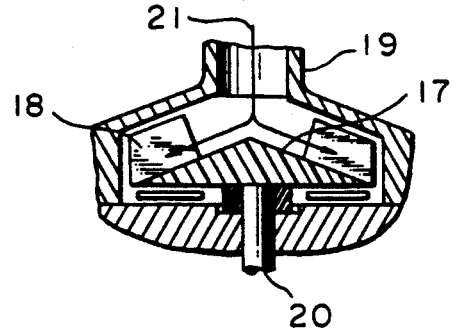
FIG. 2 is a schematic longitudinal sectional view of another type of the prior art extracorporeal blood pump.

Not only was the hemolytic test conducted under the identical conditions with those in Example 1 above with the use of the prior art blood pump of the construction shown in and described with reference to FIG. 2, but also output characteristics of the prior art blood pump were also examined. It is to be noted that the dimensions of the rotary vane assembly used in the prior art blood pump and the type of material used to construct such rotary vane assembly were identical with those of the rotary vane assembly used in the blood pump in Example 1.

Figure 11:
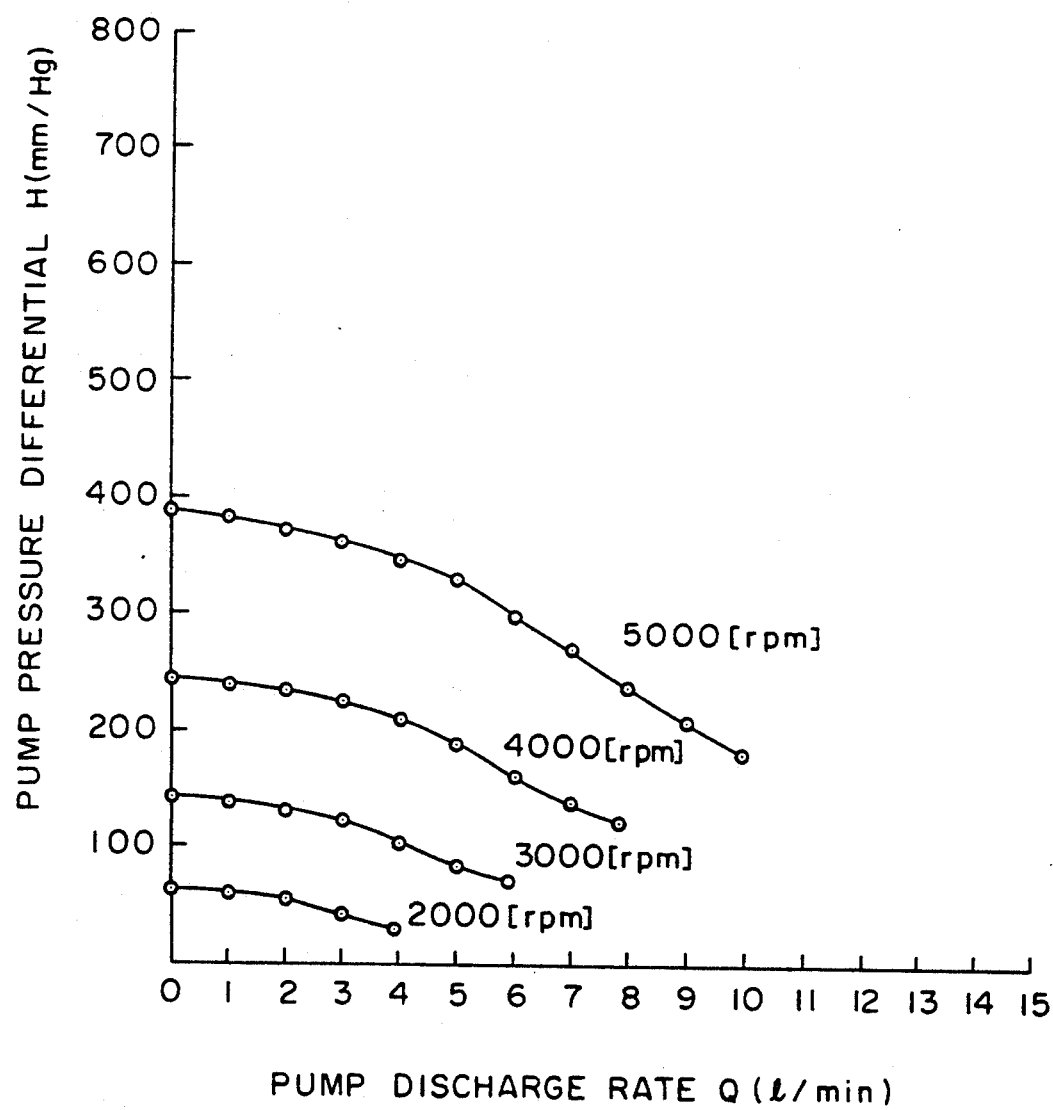
FIG. 11 is a graph showing the discharge characteristic of the prior art extracorporeal blood pump used in Comparison 2.

Results of the hemolytic test and the measured output characteristics both associated with the prior art blood pump are shown in the respective graphs of FIGS. 8 and 11.

EXAMPLE 2

Using the blood pump of the construction shown in and described with reference to FIGS. 3 to 6, another hemolytic test was conducted to determine the amount of the blood hemolyzed.

Particulars of the rotary vane assembly used in the blood pump employed for the test are as follows:

| Material | Polycarbonate resin |
|---|---|
| Pedestal Diameter R: | 50 mm |
| Pedestal Height h: | 10 mm |
| Vane Inclination Angle $\beta$: | 20 deg. |
| Vane Length/Vane Height (L/H) | 5.3 |
| Number of Vanes: | 6 |

Figure 12:
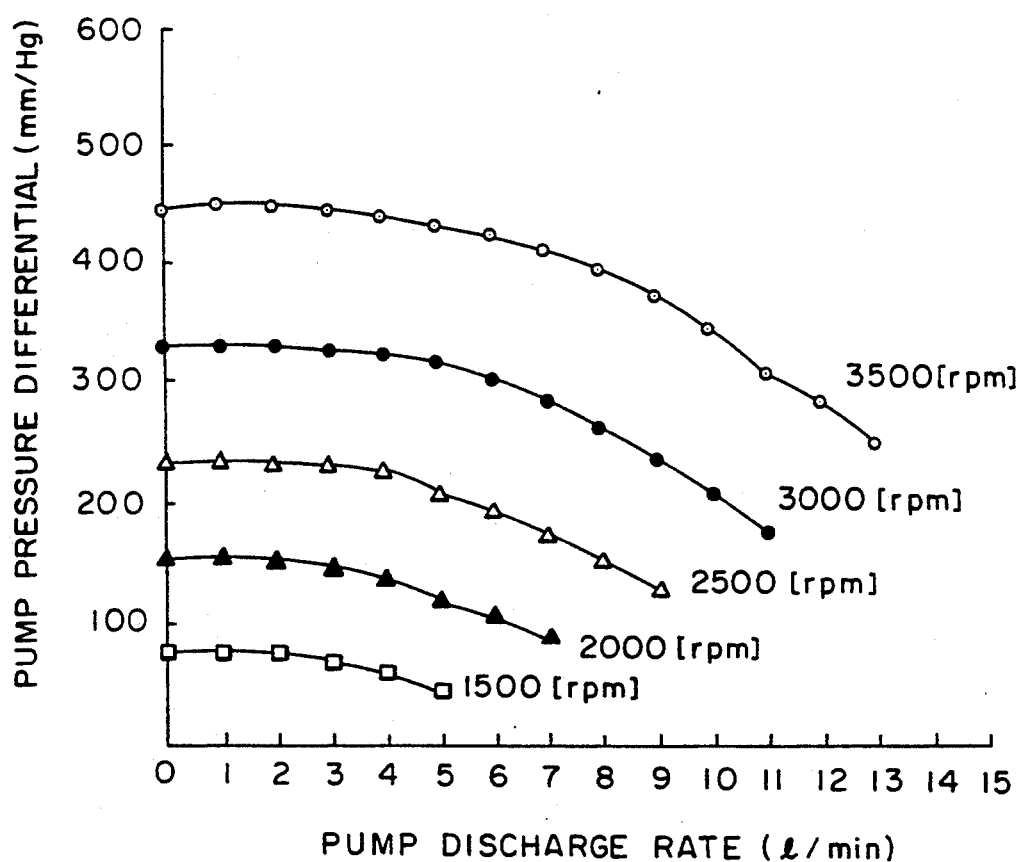
FIG. 12 is a graph showing the discharge characteristic of the extracorporeal blood pump according to the present invention.

The hemolytic test was conducted under conditions identical with those under Example 1 and the output characteristics of the blood pump were also examined. Respective results of the hemolytic test and the pump characteristic measurement are shown in the respective graphs of FIGS. 8 and 12.

Referring to the graph of FIG. 8, it is clear that, with the prior art blood pumps, the amount of the blood hemolyzed increases with a reduction in blood pumping rate, whereas with the blood pumps according to the present invention the index of hemolysis is lower than the biological tolerance of 0.1 gram per 100 liters over the entire range of 1 to 5 liters per minute.

Particularly, at a relatively low flow rate range of 2 liter per minute or less, the blood pump constructed according to the present invention exhibits a considerable reduction in amount of the blood hemolyzed as compared with the comparable prior art blood pump.

Thus, it has now become clear that, as compared with the comparable prior art blood pump, the blood pump according to the present invention is effective to satisfactorily reduce the amount of the blood which may be hemolyzed and can be safely operated over a relatively large range of flow rate.

Also, the respective graphs of FIGS. 9 to 12 make it clear that the blood pump according to the present invention is superior to the comparable prior art blood pump in respect of the pump discharge efficiency.

The blood pump of the present invention can bring about numerous advantages: (1) since the blood pump according to the present invention is of a centrifugal type, it can be manufactured compact and light weight and at a reduced cost and can be safely operated for a substantially prolonged length of time with substantially minimized possibility of malfunctioning, (2) since the blood pump according to the present invention is substantially free from occurrence of eddy currents while allowing a smooth flow of the blood, the amount of the blood which may be hemolyzed can be satisfactorily and effectively reduced, (3) the rotary vane assembly can be easily assembled or manufactured, and (4) the blood pump according to the present invention can exhibit an excellent pump discharge efficiency.

Accordingly, the blood pump according to the present invention can be advantageously used in an extracorporeal blood circulatory system such as employed in the post-operative ventricular assist device or in an artificial cardio-pulmonary device.

An embodiment of the extracorporeal blood circulatory device utilizing the blood pump of centrifugal type hereinbefore discussed in accordance with the present invention will now be described with particular reference to FIGS. 13 and 14.

Figure 13:
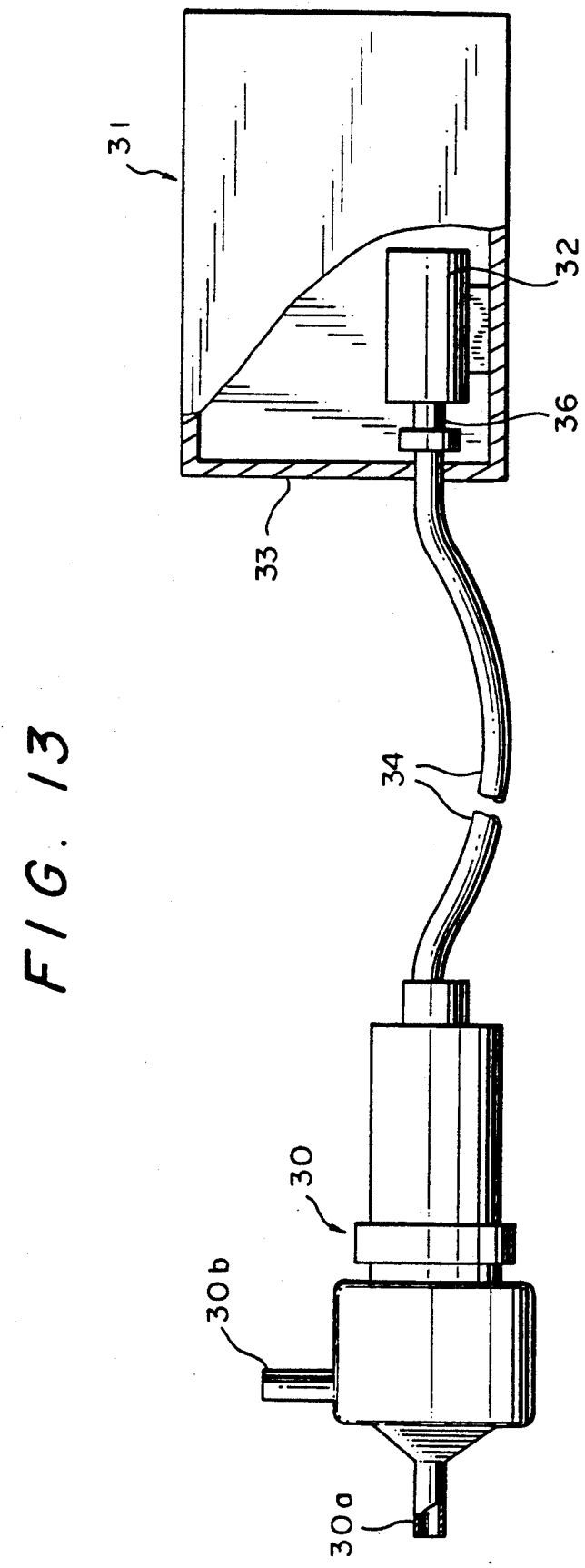
FIG. 13 is a schematic fragmentary side sectional view of a preferred embodiment of an extracorporeal blood circulatory device according to the present invention.
Figure 14:
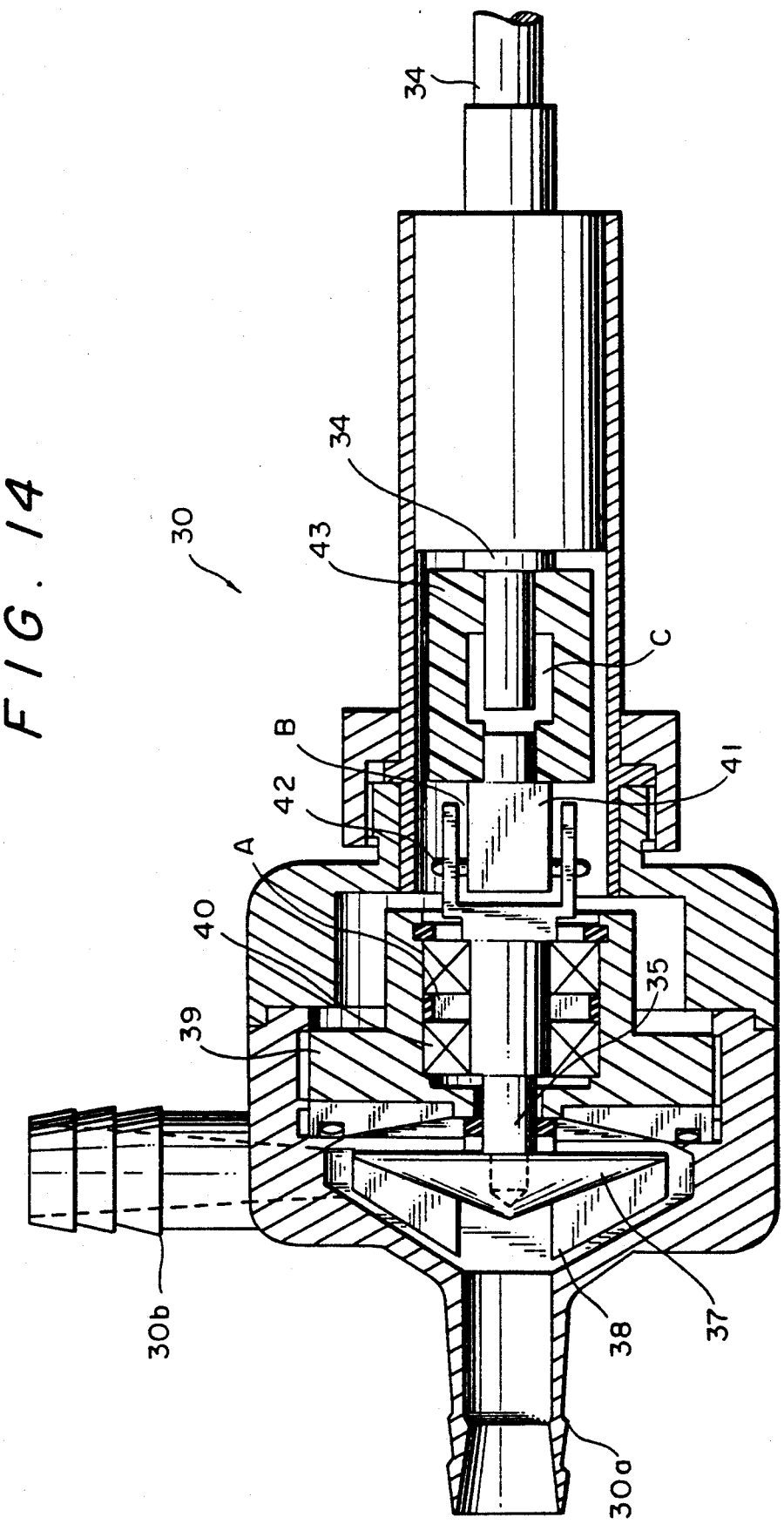
FIG. 14 is a longitudinal sectional view, on an enlarged scale, of a centrifugal blood pump used in the extracorporeal blood circulatory device shown in FIG. 13.

Referring now to FIGS. 13 and 14 showing the extracorporeal blood circulatory system according to the present invention, the blood pump of the type described hereinbefore is identified by 30, having a blood inflow port 30a coaxial with the longitudinal axis of the blood pump 30 and a blood outflow port 30b opening in a direction generally perpendicular to the longitudinal axis of the blood pump 30.

Reference numeral 31 represents a control console comprising a casing 33 in which a drive motor 32 is housed, said drive motor 32 having a drive shaft 36. Extending between the control console 31 and the centrifugal blood pump 30 is a flexible shaft 34 having one end coupled with the drive shaft 36 of the drive motor 32 and the opposite end coupled with a driven shaft 35 of the centrifugal blood pump 30.

The flexible shaft 34 is of a type comprising a flexible outer protective sheath and an internal flexible drive transmission line, for example, a coiled wire, and is freely bendable in all directions. This flexible shaft 34 may have such a length that, even though the patient's bed is located distant from the site where the control console 31 is installed, the drive shaft 36 of the drive motor 32 in the control console can be drivingly coupled with the driven shaft 35 of the blood pump 30.

As best shown in FIG. 14, a rotary vane assembly comprising a generally conical pedestal 37 having a base face and a conical face opposite to the base face and also having a plurality of vanes 38 rigidly mounted on the conical face so as to extend radially outwardly with respect to the longitudinal axis of the driven shaft 35 is rotatably accommodated within the centrifugal blood pump 30 so that, during the rotation of the rotary vane assembly about and together with the driven shaft 35, the blood entering the blood inflow port 30a can be pumped towards and subsequently discharged outwardly from the blood outflow port 30b.

The driven shaft 35 of the blood pump 30 is coaxial with the axis of rotation of the rotary vane assembly.

A free end of the driven shaft 35 remote from the rotary vane assembly is forked to have a pair of arms defining a cavity B therebetween and is drivingly connected with a generally elongated coupling element 41 inserted into the cavity B and connected releaseably with the forked arms by means of a releaseable transverse connecting pin 42. The coupling element 41 is in turn press-fitted into a thick-walled tubular coupling 43.

A generally intermediate portion of the driven shaft 35 between the rotary vane assembly and the forked arms at the free end thereof extends through a plurality of, for example, two spaced-apart bearings 40 which may be press-fitted into a cavity A defined in a generally tubular, flanged retainer 39 that is supported immovably within the pump housing at a location on one side of the rotary vane assembly opposite to the blood inflow port 30a.

In order for the thick-walled tubular coupling 43 referred to above to be pliable enough to absorb both a possible displacement in angle and an eccentric motion of the flexible shaft 34 during the drive transmission from the drive motor 32 to the rotary vane assembly in the blood pump 30, the tubular coupling 43 is not only made of flexible material of a kind capable of exhibiting a flexibility in order for the tubular coupling 43, but also has at least an outer peripheral surface formed with a multiplicity of annular grooves.

The tubular flexible coupling 43 is of an open-ended design having bearing openings defined at its opposite ends and has a generally intermediate portion of the hollow thereof having a diameter greater than that of any one of the bearing openings at the opposite ends thereof to provide a generally radially outwardly enlarged cavity C. While the coupling element 41 is press-fitted into the bearing opening at one end of the tubular flexible coupling 43, a free end of the flexible shaft 34, particularly that of the internal flexible drive transmission line, is fitted through the bearing opening at the opposite end of the tubular flexible coupling 43 so as to terminate within the radially outwardly enlarged cavity C.

Although not shown, a combination of couplings similar to the couplings 43 and 41 is to be understood as intervening between the drive shaft 36 of the drive motor 32 and the adjacent end of the flexible shaft 34, particularly that of the internal flexible drive transmission line.

Thus, it will readily be understood that, when and so long as the drive motor 32 within the control console 31 is operated, the drive of the drive motor 32 can be transmitted to the centrifugal blood pump 30 through the flexible shaft 34 to drive the blood pump 30. Conversely, when the drive motor 32 is brought to a halt, the flexible shaft 34 no longer transmits any driving force and, therefore, the centrifugal blood pump 30 is also brought to a halt.

According to the embodiment of the extracorporeal blood circulatory device hereinabove discussed, the compact centrifugal blood pump 30 and the drive motor 32 therefore are spaced a distance from each other although connected through the flexible shaft 34, the extracorporeal blood circulatory device as a whole can readily be made compact and lightweight, as compared with that in which the blood pump and the drive motor therefore are integrated together with the drive shaft of the drive motor coupled direct with the driven shaft of the blood pump.

Also, since the drive motor 32 is concealed within the control console 31 so designed and so structured as to minimize emission of noises outwardly therefrom, no buffling system such as noise shield plates or any other suitable sound attenuating material need be employed and, therefore, this feature also contributes to the manufacture of the extracorporeal blood circulatory device according to the present invention to have compact and lightweight features.

Accordingly, the extracorporeal blood circulatory device according to the present invention is easy to handle and easy to transport from place to place and can readily be installed bedside of the patient.

The patient to be treated with the extracorporeal blood circulatory device of the present invention may stay in a treatment room destant from the site where the control console housing the drive moter therein is installed. Since the control console is so designed and so structured as to, and is therefore substantially effective to, shield motor-originating noise from being emitted to the outside, the patient will not be disturbed by the motor-originating noises hitherto encountered.

Of those numerous features afforded by the present invention, an important feature is that the drive motor 32 which is apt to constitute a source of heat is distant from the centrifugal blood pump 30. This means that the hemolysis which would otherwise occur under the influence of heat-based elevated temperature can be advantageously minimized considerably.

Although the present invention has been fully described in connection with the prefferd embodiments thereof with reference to the accompanying drawings which are used only for the purpose of illustration, those skilled in the art will readily conceive numerous changes and modifications within the framework of obviousness upon the reading of the specification herein presented of the present invention. For example, so far as the extracorporeal blood circulatory device is concerned, although reference has been made to the preferred use of a combination of the detachable coupling 41 and the flexible tubular coupling 43 effective to absorb a possible angular displacement and/or an eccentric motion of the flexible shaft 34, they may be dispensed with if desired and/or if a direct coupling between the driven shaft 35 with the flexible shaft 34 serves the purpose.

Also, in the practice of any one of the foregoing preferred embodiments of the present invention, numerous modified forms of the centrifugal blood pumps have been devised and the details of, for example, the rotary vane assembly may not be always limited to those herein disclosed for the purpose of illustration of the present invention.

Accordingly, such changes and modifications are, unless they depart from the spirit and scope of the present invention as delivered from the claims annexed hereto, to be construed as included therein.

What is claimed is:

1. An extracorporeal blood pump which comprises:
   a pump housing having a pump chamber defined therein and also having blood inflow and outflow ports defined therein in communication with the pump chamber;
   a rotary vane assembly rotatably accommodated within the pump chamber and including a substantially conical rotary pedestal having a base surface and a conical surface opposite to the base surface, a plurality of generally elongated plate-like vanes each having radially inner and outer ends opposite to each other, and a driven shaft connected at one end with the base surface of the rotary pedestal;
   said plate-like vanes being mounted on the conical surface of the rotary pedestal so as to extend radially outwardly from an axis of rotation of the rotary pedestal with said radially inner ends of said respective vanes being spaced a predetermined equal distance from an apex of the shape of the conical surface of the rotary pedestal while substantially depicting a circle coaxial with the axis of rotation of the rotary pedestal, each neighboring members of said plate-like vanes being equally spaced from each other in a direction circumferentially of the rotary pedestal;
   said base surface of said rotary pedestal being of a circular shape of a diameter within the range of 30 to 55 mm enough to substantially cover a surface area of a bottom wall surface which partly defines the pump chamber and confronts said base surface of said rotary pedestal;
   each of said plate-like vanes being in the form of a straight plate of generally rectangular shape and mounted on the conical surface of the rotary pedestal so as to incline at an angle within the range of 20 to 50 degrees relative to an imaginary line tangential to the circle delimited by the radially inner ends of the respective plate-like vanes; and
   each of said plate-like vanes being so sized that the ratio L/H of the minimum height H in elevation of the radially outer end of each plate-like vane as measured in a direction parallel to the axis of rotation of the rotary pedestal relative to the length L of one of opposite side edges of such plate-like vane which is held in contact with the conical surface of the rotary pedestal is chosen to be within the range of 2.5 to 6.

2. The extracorporeal blood pump as claimed in claim 1, wherein said ratio L/H and a diameter R of said rotary pedestal satisfy the following relationships:
   $30 \leq R \leq 55$,
   $2.5 \leq L/H \leq 6$,
   $L/H \geq 0.133R - 2.33$, and
   $L/H \leq 0.133R + 0.51$.

3. The extracorporeal blood pump as claimed in claim 1, wherein said rotary pedestal has a plurality of blood flow passages each extending from the base surface to the conical surface thereof completely across the rotary pedestal.

4. The extracorporeal blood pump as claimed in claim 2, wherein said rotary pedestal has a plurality of blood flow passages each extending from the base surface to the conical surface thereof completely across the rotary pedestal.

5. An extracorporeal blood circulatory device which comprises an extracorporeal blood pump as claimed in claim 1, a drive motor positioned distant from the extracorporeal blood pump and having a drive shaft, a flexible shaft extending between the driven shaft rigid with the rotary pedestal and the drive shaft of said drive motor, and a combination of a detachable coupling and a flexible coupling effective to absorb any possible angular displacement and an eccentric motion of the flexible shaft, said combination being interposed between the drive shaft and the flexible shaft and also between the flexible shaft and the driven shaft.

* * * * *